(12) United States Patent
Warren et al.

(10) Patent No.: US 11,484,380 B2
(45) Date of Patent: *Nov. 1, 2022

(54) INTUBATION DRAPE

(71) Applicant: Encompass Group, LLC, McDonough, GA (US)

(72) Inventors: Kristy Lynn Warren, Belle Isle, FL (US); Jon Hermanson, Knoxville, TN (US); Eric Howard, Dallas, TX (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/137,869

(22) Filed: Dec. 30, 2020

(65) Prior Publication Data

US 2022/0061951 A1   Mar. 3, 2022

Related U.S. Application Data

(60) Provisional application No. 63/069,963, filed on Aug. 25, 2020.

(51) Int. Cl.
| | | |
|---|---|---|
| *A61B 46/20* | (2016.01) | |
| *A61B 90/00* | (2016.01) | |
| *A61B 46/00* | (2016.01) | |
| *A61M 16/04* | (2006.01) | |

(52) U.S. Cl.
CPC .............. *A61B 90/05* (2016.02); *A61B 46/20* (2016.02); *A61B 46/40* (2016.02); *A61M 16/0488* (2013.01)

(58) Field of Classification Search
CPC ......... A61B 46/23; A61B 46/30; A61B 46/40; A61B 2046/201; A61B 2046/205; A61B 2046/234; A61B 46/20; A61B 90/05; A61B 90/40; A61M 16/0488; A61G 10/00; A61G 10/005; A61G 10/02; A61G 10/04

See application file for complete search history.

(56) References Cited

U.S. PATENT DOCUMENTS

| | | | | |
|---|---|---|---|---|
| 2,683,262 | A * | 7/1954 | Foss ........................... | G21F 3/02 2/457 |
| 3,096,759 | A * | 7/1963 | Coolbaugh ............. | A61F 17/00 2/84 |
| 4,922,562 | A * | 5/1990 | Allred .................... | A61G 1/013 5/628 |
| 4,998,296 | A * | 3/1991 | Stames .................. | A41D 15/04 2/84 |
| 7,766,950 | B2 * | 8/2010 | Castellani ................. | A61F 7/03 607/108 |
| 2002/0157184 | A1* | 10/2002 | Maturaporn ......... | A47G 9/0223 5/482 |
| 2022/0008275 | A1* | 1/2022 | Villa .................... | A61G 10/005 |

* cited by examiner

*Primary Examiner* — Camtu T Nguyen
(74) *Attorney, Agent, or Firm* — Baker, Donelson, Bearman, Caldwell & Berkowitz, PC; Dorian B. Kennedy

(57) ABSTRACT

A medical drape which is positioned over the head and upper torso of a patient is disclosed which includes a head flap, a head portion, a torso portion, and two oppositely disposed arm portions. The head flap is of a sufficient length to extend about the backside of the patient=s head. The head portion includes oppositely disposed side wings which aid in covering the head of a patient. Each arm portion includes an access slot extending through the arm portion.

12 Claims, 1 Drawing Sheet

INTUBATION DRAPE

CROSS REFERENCE TO RELATED APPLICATIONS

Applicant claims the benefit of U.S. Provisional Patent Application Ser. No. 63/069,963 filed Aug. 25, 2020 and entitled INTUBATION DRAPE.

STATEMENT REGARDING FEDERALLY SPONSORED RESEARCH OR DEVELOPMENT

Not applicable.

The Names of the Parties to a Joint Research Agreement

Not applicable.

FIELD OF THE INVENTION

The present inventive concept relates to the field of medical drapes. More particularly, the invention relates to a medical drape used during the intubating or extubating of a patient.

BACKGROUND OF THE INVENTION

Oftentimes, medical personnel must intubate a patient in order to secure a proper airway for the patient or extubate in order to remove an intubation tube from a patient=s airway. During the intubation process medical instruments are placed into the mouth and throat of a person to allow a clear view of the airway for positioning an intubation tube. This process creates airborne particles or an aerosol that may contain pathogens, such as bacterium, viruses or other micro-organisms. The airborne pathogen poses a significant risk to the medical personnel performing the procedures.

To prevent the spread of such airborne pathogens, barriers have been used to contain the patient=s head. One such device has been the use of a box with internal sleeves that is placed over the head of a patient during the medical procedure. The box is made of a clear plastic so that the medical personnel may view the process. A problem with such devices is that the box must be stored when not in use. Another problem is that the box is intended to be re-usable, therefore, the box must be decontaminated after each use.

Another improvised method of limiting exposure has been through the use of a clear conventional rain poncho. The hood of the rain poncho is placed over the face of a patient while the body of the poncho is laid upon the patient=s chest. While the use of a poncho may cover the face of a patient during the procedure, the poncho may easily slide out of place during the procedure. Also, the poncho does not properly contain the airspace around the patient=s face during the removing of the poncho from the patient. Lastly, the poncho requires the medical personnel to insert, extract, and move his or her hands beneath the entire poncho during the medical procedure, which may cause the poncho to slip out of place or may create a breach of the air pocket between the patient and the overlying poncho.

Accordingly, a need exists for a medical drape that may be used during the intubation or extubating of a patient that allows a clear view of the medical field while also allowing unobstructed movement of the medical personnel and instruments while also substantially containing the airspace after the procedure. It is to the provision of such therefore that the present invention is primarily directed.

SUMMARY OF THE INVENTION

An intubation drape comprises a flexible sheet of clear plastic material having a torso portion and a head portion extending from the torso portion. The torso portion has two oppositely disposed arm portions extending from the torso portion. Each arm portion has an access slot extending therethrough. With this construction, the intubation drape is positioned over a patient with the torso portion over the torso of the patient and the head portion over the face of a patient.

BRIEF DESCRIPTION OF THE DRAWINGS

So that the manner in which the present inventions can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

DETAILED DESCRIPTION OF CERTAIN EMBODIMENTS

Figure 1:
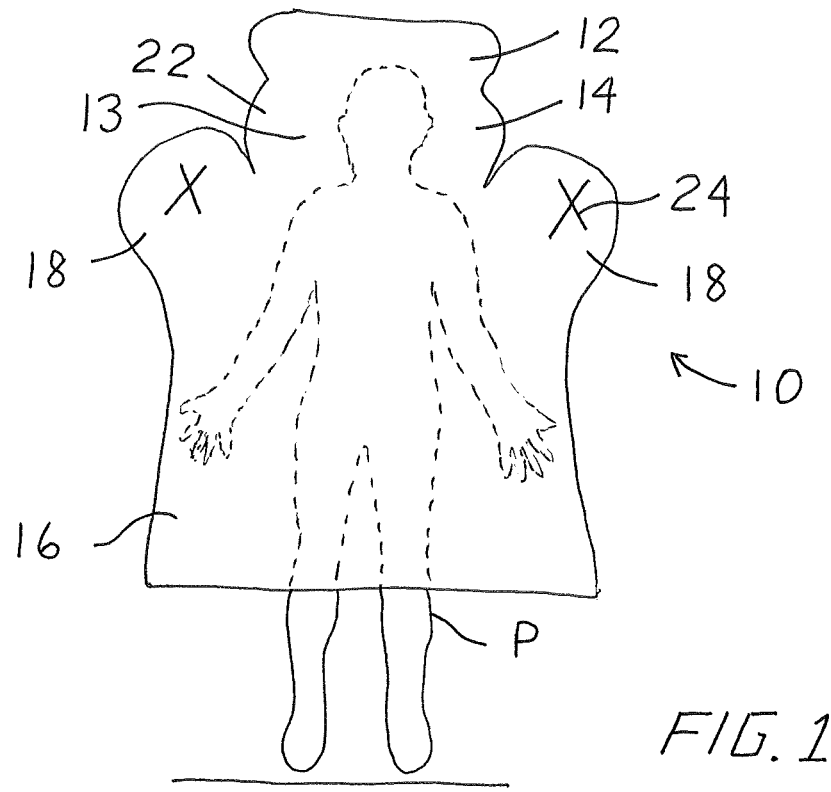
FIG. 1 is a plan view of an intubation drape embodying principles of the invention in a preferred form, shown in an initial, unmounted position upon a patient.

With reference next to the drawings, there is a shown a surgical or medical intubation or extubating drape 10 in a preferred form of the present invention, referenced herein as drape 10. The drape 10 is configured to be positioned over the head and upper torso of a patient P, and may be used for other medical procedures besides those specifically recited herein.

The drape 10 is a generally thin, flat film, layer, or sheet of clear, flexible material, such as a sheet of thin plastic material. The drape 10 is shaped to include a head portion 14 and a torso portion 16. The head portion 14 has a face portion 13 and a head extension, extension flap, or flap 12 extending from the face portion 13 oppositely disposed from the torso portion 16. The torso portion 16 has two oppositely disposed and outwardly extending arms or arm portions 18.

Figure 2:
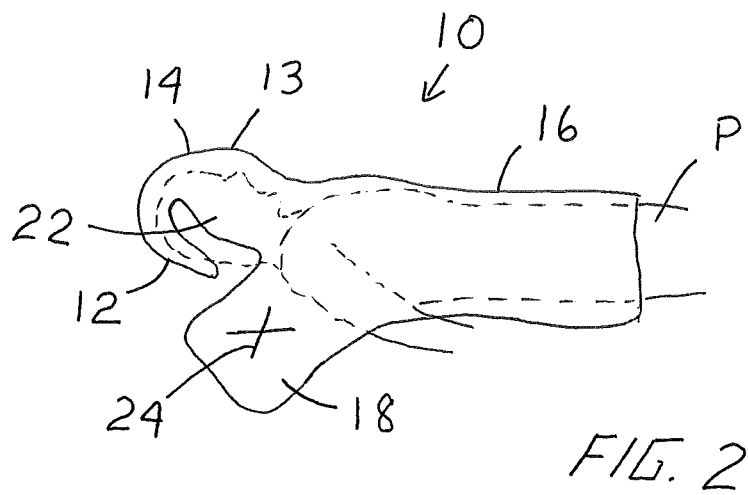
FIG. 2 is a side view of the intubation drape of FIG. 1, shown in a mounted position upon a patient.

The head flap 12 extends from the upper portion of the head portion 14. The head flap 12 is of a sufficient length to extend about the backside of the patient=s head with the head portion 14 laying upon the patient=s face, as shown in FIG. 2. As such, the head flap 12 anchors or maintains the face portion 13 in a position upon the face of the patient through the weight of the patient=s head upon the flap 12.

The head portion 14 includes oppositely disposed side bulges or wings 22 which aid it covering the head of a patient and extending the width of the face portion 13. The wings 22 also allow air to enter below the head portion 14 in the area of the patient=s neck to allow the patient to breathe.

Each arm portion 18 includes an access slot 24 extending through the arm portion 18. The access slot 24 may be in the form of two intersecting slits to form an X-shaped slit, cut or slot extending through the plastic material of the arm portions 18, i.e., extending from the top surface to the bottom surface of the sheet material that forms the arm portions 18.

In use, with the patient P in a supine position upon a support surface, the drape 10 is placed upon the patient P with the head portion 14 positioned over the patient=s face and the torso portion 16 positioned over the patient=s torso with the arm portions 18 extending laterally to the sides. The head flap 12 is then tucked under or below the patient=s head so that the weight of the patient=s head maintains the position of the head flap 12 and consequently the entire head portion 14, as shown in FIG. 2.

The medical personnel may then slide medical instruments below the head portion 14 of the drape 10. The medical personnel=s arms are then inserted through the arm access slots 24 within the arm portions 18, so that the medical personnel=s hands may manipulate the medical instruments into position to perform the intubation or extubating of the patient. The medical personnel=s hands easily slide through the access slots 24 due to the access slot 24 comprising two slits in two different directions that ensure an opening of the slot, and thus preventing a closing of the slit should the hands initially contact the arm portions 18 in a position just off the access slots 24 that may cause the access slot 24 to close somewhat due to a pulling of the material. The drape 10 creates an air pocket above the patient=s face which prevents airborne particles from escaping the area about the patient=s face below the confines of the drape 10. As the drape is made of a clear material, the medical personnel may view the medical field through the drape 10, and especially the face portion 13.

Once the procedure has concluded, the medical instruments are removed from the medical field and the medical personnel=s arms are withdrawn from the arm access slots 24. The face portion 13 and flaps 12 of the drape 10 may then be gathered around the patient=s head to extend the pocket over the patient=s face and then closed by bunching the head portion 14 directly over the patient=s face, to essentially capture the airspace over the patient=s face within the confines of the gathered drape 10, i.e., a pocket is created to capture the air about the patient=s face. It should be noted that the configuration of the side wings 22 aids in providing additional material for the gathering and formation of the pocket during this part of the drape removal process. The presence of the flap 12 between the patient=s head and the underlying support surface aids in maintaining the position of the face portion 13, and thus the entire drape 10, so that it does not slide down during the medical procedure or during the drape removal process thereafter. By gathering the airspace over the patient=s face, the drape 10 aids in preventing airborne pathogens from escaping into the atmosphere. The gathered drape 10 may then be disposed of according to proper medical protocols.

It should be understood that the drape may be formed with only the head portion 12, and especially the face portion 13, made of a clear material. However, this is not preferred as the formation of the drape through a single layer is believed to provide a uniform construction without seams that may create an air leak in not formed correctly.

It should be understood that the access slots 24 may be in any form which allows the passage of a person=s arms through the access slots 24. However, it is believed that the X-shaped slit provides a great benefit over a single slit or slot that may tend to close upon the arm. The X-shaped slit and its position on the arm portion 18 allows the hands and forearms of the medical personnel to enter and exit the drape with a minimum of snagging, thus reducing the chances of the drape being improperly removed or the airspace about the patient=s face from breaching during the gathering procedure. Alternatively, the access slots 24 may be in the form of two intersecting slits, which may form a Y-shape slit or T-shaped slit. It should be understood that each slit may also be curved instead of the straight slits shown in the drawings.

As such, an intubation drape 10 includes a flexible sheet of clear plastic material having a torso portion, a head portion extending from the torso portion, and a head flap extending from the head portion oppositely disposed from the torso portion with respect to the head portion. The drape also has arm portions with access slots to enable medical personnel to pass their hands through the drape with minimal pulling of the drape material. With this construction, the intubation drape is positioned over a patient with the torso portion over the torso of the patient, the head portion over the face of a patient, and the head flap under the head of the patient.

Variations of intubation the drape may fall within the spirit of the claims, below. It will be appreciated that the inventions are susceptible to modification, variation, and change without departing from the spirit thereof.

The invention claimed is:

1. An intubation drape comprising:
a flexible sheet of clear plastic material having a torso portion and a head portion extending from said torso portion, said torso portion having two oppositely disposed arm portions extending from said torso portion, each of said disposed arm portions has an access slot extending therethrough,
whereby the intubation drape is adapted to be positioned over a patient with the torso portion over the torso of the patient and the head portion over the face of the patient.

2. The intubation drape of claim 1 wherein each said access slot is an X-shaped slit extending through each of said disposed arm portions.

3. The intubation drape of claim 1 wherein each said access slot is formed by two intersecting slits.

4. The intubation drape of claim 1 further comprising a head flap extending from said head portion oppositely disposed from said torso portion with respect to said head portion.

5. The intubation drape of claim 1 further comprising two oppositely disposed wings extending from said head portion.

6. The intubation drape of claim 4 further comprising two oppositely disposed wings extending from said head portion.

7. An intubation drape comprising:
a unitary, clear, flexible sheet having,
a torso portion,
a face portion extending from said torso portion, and
a pair of oppositely disposed arm portions extending laterally from said torso portion, each of said disposed arm portions has an arm slit extending through said arm portion,
whereby the intubation drape is adapted to be positioned over a patient with the torso portion over the torso of the patient, the face portion over the face of the patient, and the arm slits adapted to allow medical personnel access to the patient through the intubation drape.

8. The intubation drape of claim 7 wherein each said access slit is an X-shaped slit extending through each of said disposed arm portions.

9. The intubation drape of claim 7 wherein each said access slit is formed by two intersecting slits.

10. The intubation drape of claim 7 further comprising a head flap extending from said head portion oppositely disposed from said torso portion with respect to said head portion.

11. The intubation drape of claim 7 further comprising two oppositely disposed wings extending from said head portion.

12. The intubation drape of claim 10 further comprising two oppositely disposed wings extending from said head portion.

\* \* \* \* \*